United States Patent [19]
Miles et al.

[11] Patent Number: 5,188,100
[45] Date of Patent: Feb. 23, 1993

[54] APPARATUS FOR FACILITATING TRACHEOSTOMY TUBE REPLACEMENT

[75] Inventors: Richard Miles; Stephen G. Rothstein, both of New York, N.Y.

[73] Assignee: New York University, New York, N.Y.

[21] Appl. No.: 756,681

[22] Filed: Sep. 9, 1991

[51] Int. Cl.$^5$ .......................................... A61M 16/04
[52] U.S. Cl. ........................ 128/207.14; 128/207.17; 128/200.26; 128/911; 604/264
[58] Field of Search ...................... 128/200.26, 207.14, 128/207.15, 207.16, 207.17, 207.29, 911, 912; 624/264

[56] References Cited

U.S. PATENT DOCUMENTS

| | | |
|---|---|---|
| 2,024,982 | 12/1935 | Scott . |
| 3,606,669 | 9/1971 | Kemble . |
| 3,721,229 | 3/1973 | Panzer . |
| 3,913,565 | 10/1975 | Kawahara ...................... 128/207.15 |
| 4,246,897 | 1/1981 | Muto . |
| 4,329,983 | 5/1982 | Fletcher ...................... 128/207.15 X |
| 4,340,046 | 7/1982 | Cox . |
| 4,705,041 | 11/1987 | Kim . |
| 4,824,435 | 4/1989 | Geisy et al. . |
| 4,889,112 | 12/1989 | Schachner et al. . |
| 4,909,248 | 3/1990 | Anderson . |
| 4,960,122 | 10/1990 | Mizus . |
| 5,058,580 | 10/1991 | Hazard ...................... 128/200.26 X |
| 5,060,645 | 10/1991 | Russell ...................... 128/200.26 X |

FOREIGN PATENT DOCUMENTS 0407663 1/1991 European Pat. Off. ........ 128/207.15

OTHER PUBLICATIONS

Browne, D. R. G., "A Guide to Tracheal Tubes", *Anaesthesia*, 24(4):620–622 (1969).
Harley, W. T. et al., "Fabrication of Tracheotomy Obturators", *J. Prosth. Dent.,* 25(6): 679–683 (1971).
Kowaleski, H. et al., "Guide-Wire Perforation During Bougienage and Tube Positioning", *Endoscopy*, 20(6): 332–333 (1989).
McQuarrie, D. G., "Safe Replacement of Tracheostomy Tubes", *Surg. Gynecol. Obstet.,* 140(5):769–770 (1975).
Seitz, P. A. et al., "Endobronchial Rupture from Endotracheal Reintubation with an Endotracheal Tube Guide", *J. Clin. Anesth.,* 1(3):214–217 (1989).
Sit, K.-F. et al., "Alternative Antegrade Method for Endotracheal Tube Replacement", *Anesth. Sinica.,* 26(4): 417–422 (1988).
Tobias, R., "Increased Success with Retrograde Guide for Endotracheal Intubation", *Anesth. Analg.,* 62:366–371 (1983).

*Primary Examiner*—V. Millin
*Assistant Examiner*—Raleigh W. Chiu
*Attorney, Agent, or Firm*—Browdy and Neimark

[57] ABSTRACT

An apparatus for carrying out tracheostomy tube replacement includes the use of a specially constructed obturator having a central longitudinal opening. The central opening of the obturator allows the obturator to pass over a guide tube which has been left in place after removal of the old tracheostomy tube. The obturator also has an atraumatic rounded tip to make passage of the obturator and replacement tracheostomy tube assembly through the stoma and into the tracheal lumen safer and easier, guided by the emplaced guide tube.

4 Claims, 1 Drawing Sheet

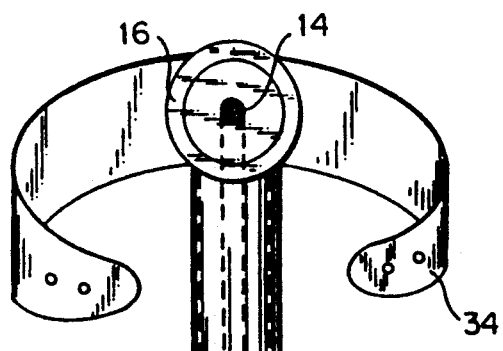
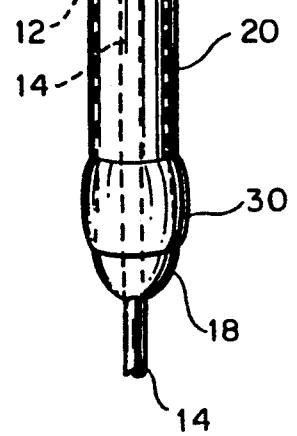
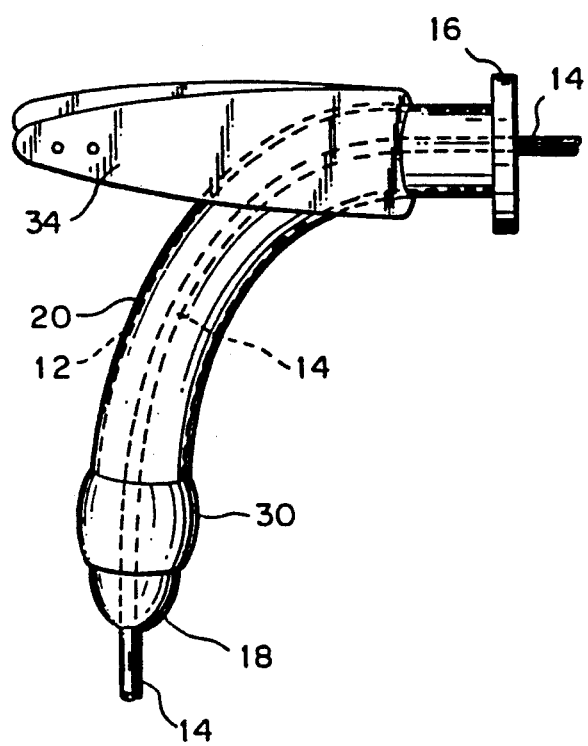
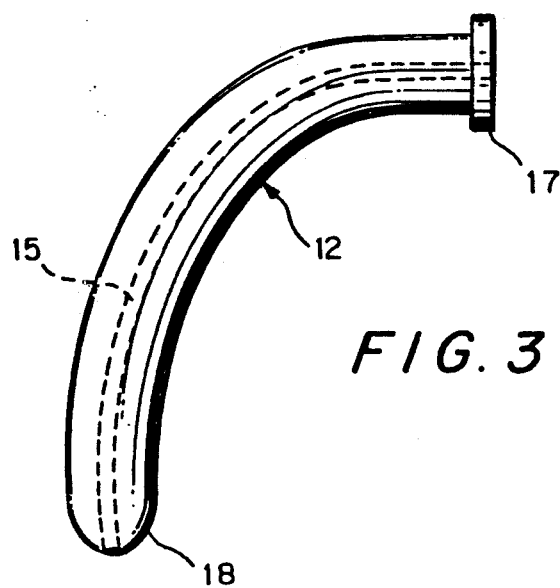

APPARATUS FOR FACILITATING TRACHEOSTOMY TUBE REPLACEMENT

FIELD OF THE INVENTION invention relates to medical devices and, more particularly, to an improved tracheostomy tube obturator having a central longitudinal opening for passing a guide tube for improved replacement of tracheostomy tubes. The present invention also relates to a tracheostomy kit including such an obturator and the method of replacing a tracheostomy tube using the obturator and guide tube of the present invention.

BACKGROUND OF THE INVENTION

Tracheostomy is a common surgical procedure involving the surgical creation of an opening into the trachea through the neck for insertion of a tube to facilitate the passage of air to the lungs or the evacuation of secretions. Tracheostomy is usually done to provide an adequate airway for prolonged ventilatory support, to bypass obstruction of the upper part of the respiratory tract and for pulmonary toilet.

Tracheostomy tubes are usually made of plastic such as polyethylene. All are curved to accommodate the anatomy of the trachea. The plastic tracheostomy tubes presently in use have an inflatable cuff attached. The inflatable cuff is built on the outer surface of the cannula. The purpose of the cuff is to hold the tube in place and prevent the flow of air around the outside of the cannula. This allows for more effective ventilation of the patient and prevents the aspiration of liquids and foods into the trachea. Tracheostomy tubes may consist of single or double cannulas. Double cannula tubes include an outer cannula to maintain the patency of the airway and an inner cannula that fits snugly inside the outer cannula and can be removed for cleaning and removal of accumulated secretions without disturbing the operative site.

An accessory to tracheostomy tubes is the obturator or pilot, which is an olive tipped curved rod that is placed within the tracheostomy tube so that its atraumatic tip extends just forward of the distal end of the tracheostomy tube. The tip of the obturator is used to guide the tracheostomy tube into the trachea and prevent damage to the tracheal walls while the tube is being inserted. Once the tracheostomy tube has been inserted, the obturator has served its purpose and it is removed from the center of the tracheostomy tube.

A significant problem with present tracheostomy tubes is the difficulty which attends the change of the tracheostomy tube or replacement of a dislodged tube. Substantial problems may occur, for example, in replacing tracheostomy tubes in obese patients, in the patient with a recent tracheostomy, and in patients with scarring in the area. The airway is essential. If the tube is dislodged, the soft tissue surrounding the tracheostomy wound obstructs the airflow, preventing the patient from breathing. During the period between removal of the old tube and insertion of the new tube, access to the tracheal area can constrict or may have already become so edematous that insertion of the new tube may be difficult or impossible because of inadequate anatomic definition. Thus, the method of reintubation may expose the patient to risks of bleeding, trauma, airway perforation, or loss of airway which may add potential complications to the procedure or lead to death.

Another significant error which can occur, is the placement of the tube in the pretracheal space in which the inflated cuff blocks the airway and the mediastinum is insufflated with air from a respirator. Such an error compromises venous return while failing to maintain adequate oxygen exchange. Continuing forceful attempts to replace the tube compresses the trachea and blocks any air exchange. In obese patients, shorter tracheostomy tubes may not be advanced far enough into the trachea and may dislodge to the pretracheal space when the patient's head is repositioned.

These inherent risks would potentially expose the patient to inadequate ventilation, oxygenation and/or airway control during this period of loss of function and the presence of the tracheostomy tube. In a situation where a patient requires a tracheostomy tube to assist in a patient's life support system, any delay may present potentially serious complications and/or death. In addition, tracheal tube replacement is considered a procedure carrying a degree of associated risk whose completion requires highly trained practitioners.

Thus, efficient ways of replacing or changing a tracheostomy tube have been sought which avoid problems of tracheal ulcer and damage and permits insertion directly into the trachea.

In McQuarrie, "Safe Replacement of Tracheostomy Tubes", *Surgery, Gynecology and Obstetrics*, 140, 769-770 (1975), several methods useful in the routine management of tracheostomies are disclosed among which is the use of a catheter as a guide tube. This reference discloses that when changing the tube in a new tracheostomy, a suction catheter can be inserted through the tube to be removed. The tube is then removed over the catheter, leaving a good length of the catheter in the trachea. The new tracheostomy tube may then be slid into proper position over the catheter. U.S. Pat. No. 4,960,122 to Mizus also discloses use of such a guide tube. These methods, however, are not without drawbacks as the conventional obturator cannot be used and the opening into the trachea may be scarred, torn or distorted, preventing the new tracheostomy tube from being inserted into the trachea over the guide.

SUMMARY OF THE INVENTION

It is an object of the present invention to provide a system for replacement of a tracheostomy tube which overcomes and eliminates the problems and deficiencies of the prior art.

It is another object of the present invention to provide such a system for replacement of a tracheostomy tube in an already intubated patient that may be accomplished in a safe and expedient manner.

It is a further object of the present invention to provide a device which reduces the risks of bleeding trauma, airway perforations and loss of airway while eliminating the risk of tracheostomy intubation or control of airway access.

It is yet another object of the present invention to provide a novel method of replacement of a tracheostomy tube.

It is still a further object of the present invention to provide an obturator which may be used during reintubation or changing of a tracheostomy tube which facilitates the use of a guide tube or other elongated guide means.

It is yet a further object of the present invention to provide a tracheostomy kit which includes the devices necessary to practice the method of the present invention.

The above and other objects and advantages of the present invention are achieved by a specially constructed obturator device and a method for its use. The obturator of the present invention has a hollow core permitting passage through the obturator of a hollow flexible plastic tube which acts as a guide. The obturator of the present invention is used by inserting the guide tube through a tracheostomy tube in need of replacement, which is typically already in position in the tracheal lumen of the patient. The old tracheostomy tube is removed from the patient over the guide tube, leaving the guide tube in position in the tracheal lumen. The replacement tracheostomy tube with the obturator of the present invention in place, which has a round blunted tip to facilitate safe and easy passage, is progressed over the guide tube, where it is advanced to a desired position. The opening through the core of the obturator permits it, and the tracheostomy tube, to slide over the guide tube. The guide tube and the obturator of the present invention can then be removed, leaving the replacement tracheostomy tube in position in the lumen.

BRIEF DESCRIPTION OF THE DRAWINGS

The above and other objects and advantages of the present invention will become apparent in the following detailed description of the preferred embodiments when read in conjunction with the attached drawings, in which:

FIG. 1 is a schematic representative rear view of a tracheostomy tube with the specially constructed obturator of the present invention and a guide tube in place for use in accordance with and as part of the present invention;

FIG. 2 is a schematic representative side view of the obturator, tracheostomy tube and guide tube of FIG. I; and FIG. 3 is a longitudinal cross-section of the obturator of the present invention.

DETAILED DESCRIPTION OF THE PREFERRED EMBODIMENTS

The apparatus and method in accordance with the present invention will be described with reference to FIGS. 1 to 3. While the tracheostomy tube and obturator of the present invention may be used without the guide tube for initial intubation of a patient, the primary purpose of the invention is for the replacement of an existing tracheostomy tube in an intubated patient with a new tracheostomy tube. Referring now to FIGS. 1 and 2, a standard tracheostomy tube 20 may be used with a flange 16 at the proximal end and an inflatable annular cuff 30 at the distal end. Wings 34 are fixed to the tube 20 near the proximal end thereof for securing the tube to the patient. The inflatable cuff 30 is coupled to a syringe connector by means of a tube (not shown) disposed in the wall of the tracheostomy tube 20.

The obturator 12 for use with the present invention is shown in FIG. 3. The obturator 12 is substantially cylindrical and is made of a plastic material sufficiently flexible to permit it to easily assume the shape of the curved tracheostomy tube 20. The distal tip 18 of the obturator 12 is rounded or olive-tipped. At the proximal end of the obturator 12, there is disposed a flange 17.

The length of the obturator 12 is specifically selected so that when inserted into the tracheostomy tube 20 such that the flange 17 of the obturator 12 abuts the flange 16 of the tracheostomy tube 20, as shown in FIGS. 1 and 2, the rounded tip 18 will extend from the distal end of the tube 20. Thus, the rounded tip 18 of the obturator functions as an atraumatic guide tip to the distal end of the tracheostomy tube and serves to guide the tube and prevent tracheal damage which might otherwise be caused by the distal edges of the tracheostomy tube 20.

The obturator 12 has a longitudinal opening 15 centrally disposed therethrough. The central opening is large enough to allow a guide tube 14 (see FIGS. 1 and 2) to pass therethrough. The guide tube 14 and the central opening 15 must be sized so that the obturator 12 can easily slide over the guide tube 14 when the guide tube 14 is passed through the central opening 15.

The guide tube 14 is preferably a flexible plastic catheter suction tube which may be used, if desired, for aspirating secretions or for administering oxygen during the removal and replacement of the main tracheostomy tube. It should be understood, however, that the guide tube 14 may be a solid flexible tube, more in the nature of a guide wire, as long as it is not so sharp as to cause damage to the trachea during its insertion.

The procedure in accordance with the present invention for replacing a tracheostomy tube which is already in place on a patient, is made safe, and expedient by means of the apparatus of the present invention. When the tracheostomy tube 20 is in place in the patient with the cuff 30 inflated so as to seal the trachea, a guide tube 14 is fed through the tracheostomy tube 20 to be removed. The tube 14 is fed far enough to leave a good length of the guide tube 14 in the trachea when the tracheostomy tube 20 is removed. The cuff 30 is then deflated with an appropriate syringe. The tracheostomy tube 20 is then removed over the guide tube 14 leaving the guide tube 14 in place in the trachea to serve as a guide to the existing opening to the trachea. An obturator 12 is inserted within a new tracheostomy tube 20 such that obturator flange 17 abuts tracheostomy tube flange 16 and the rounded end 18 of the obturator extends from the distal end of the tracheostomy tube 20. The proximal end of the guide tube 14 is threaded through the central opening 15 of the obturator 12 by means of the tip 18 and the entire obturator 12—tracheostomy tube 20 assembly is fed over the guide tube 14 so as to be guided into position through the existing opening in the trachea using guide tube 14 as a guide. The rounded tip 18 of the obturator serves to center the tracheostomy tube 20 within the tracheal lumen and to guide it into place atraumatically. Once the obturator tube 20 is secured in place, the obturator 12 and the guide tube 14 are removed from the tracheostomy tube 20. The cuff 30 is then inflated and its position verified in a routine manner.

The foregoing description of the specific embodiments will so fully reveal the general nature of the invention that others can, by applying current knowledge, readily modify and/or adapt for various applications such specific embodiments without departing from the generic concept, and, therefore such adaptations and modifications should be and are intended to be comprehended within the meaning and range of equivalents of the disclosed embodiments. It is to be understood that the phraseology or terminology employed herein is for the purpose of description and not of limitation.

What is claimed is:

1. An obturator for use with a tracheostomy tube to facilitate replacement of the tracheostomy tube, comprising:

a substantially cylindrical body having a distal end, intended to extend from the distal end of the tracheostomy tube when in use, and a proximal end, intended to extend from the proximal end of the tracheostomy tube when in use, said body being sufficiently flexible to permit it to easily assume the shape of the tracheostomy tube with which the obturator is intended to be used;

a blunt, rounded, atraumatic tip disposed at the distal end of said body;

a flange disposed at the proximal end of said body, the length of said body being selected such that when said flange abuts the proximal end of the tracheostomy tube with which the obturator is intended to be used, said tip extends from the distal end of the tracheostomy tube far enough to effectively form a blunt, rounded, atraumatic end to the tracheostomy tube;

wherein a central longitudinal opening extends throughout said cylindrical obturator body, including said tip and said flange, such that, when in use, a guide tube can be inserted through the obturator by means of said opening.

2. A tracheostomy kit, comprising:

a tracheostomy tube; and an obturator in accordance with claim 1, sized and dimensioned for use with said tracheostomy tube.

3. A tracheostomy kit in accordance with claim 2, further including guide means, sized and dimensioned to permit passage through said opening in said obturator, for placement through a tracheostomy tube in place on a patient so as to guide the reemplacement of a new tracheostomy tube, when in use.

4. A tracheostomy kit in accordance with claim 3, wherein said guide means comprises a suction catheter.

* * * * *